US012385818B2

United States Patent
Abdelrahman et al.

(10) Patent No.: US 12,385,818 B2
(45) Date of Patent: Aug. 12, 2025

(54) MODELING GAS DESORPTION IN A SUBSURFACE RESERVOIR

(71) Applicant: Saudi Arabian Oil Company, Dhahran (SA)

(72) Inventors: Moemen A. Abdelrahman, Dhahran (SA); Belaifa Elhadi, Dhahran (SA); Zhen Chen, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 372 days.

(21) Appl. No.: 18/109,598

(22) Filed: Feb. 14, 2023

(65) Prior Publication Data
US 2024/0272057 A1    Aug. 15, 2024

(51) Int. Cl.
*G01N 7/14*     (2006.01)
*E21B 43/00*    (2006.01)
(Continued)

(52) U.S. Cl.
CPC ............ *G01N 7/14* (2013.01); *G01V 11/00* (2013.01); *E21B 43/006* (2013.01)

(58) Field of Classification Search
CPC ............ G01N 7/14; G01N 2203/006; G01N 2203/0067; G01N 33/241; G01N 2015/0873; G01N 7/04; G01N 5/02; G01N 31/12; G01N 33/005; G01N 33/2025; G01N 1/28; G01N 2030/8872; G01N 30/02; G01N 30/86; G01N 30/8693; G01N 33/1813; G01N 33/182; G01N 33/1826;
(Continued)

(56) References Cited

U.S. PATENT DOCUMENTS 10,156,507 B2 *  12/2018  Davidson ........... G01N 15/0893
11,014,829 B2     5/2021  Parthasarathy
(Continued)

FOREIGN PATENT DOCUMENTS

AU    2008265701    12/2008
AU    2020103953    2/2021
(Continued)

OTHER PUBLICATIONS

Pathi et al., "Limited storage and recovery of adsorbed gas in shale reservoirs—Insights from experiments and production modeling," Fuel Communications, Mar. 2022, 10:100059, 12 pages.
(Continued)

*Primary Examiner* — Andre J Allen
(74) *Attorney, Agent, or Firm* — Fish & Richardson P.C.

(57) ABSTRACT

Systems and methods for modeling gas desorption in a subterranean reservoir include measuring a gas sorption parameter using a crushed core sample from the subterranean reservoir; computing a gas storage capacity of the subterranean reservoir at an initial reservoir pressure based on the gas sorption parameter; generating a three-dimensional (3D) distribution of total organic carbon (TOC) in the subterranean reservoir; estimating a 3D distribution of original adsorbed gas in place of the subterranean reservoir by correlating the gas storage capacity with the 3D distribution of TOC; and predicting the amount of gas desorbed from the subterranean reservoir as the reservoir is depleted.

20 Claims, 6 Drawing Sheets

(51) Int. Cl.
*G01V 11/00* (2006.01)
*G01V 20/00* (2024.01)

(58) Field of Classification Search
CPC .... G01N 33/222; G01N 33/225; G01N 33/24; E21B 43/006; E21B 43/2401; E21B 47/07; E21B 36/00; E21B 36/001; E21B 36/02; E21B 36/04; E21B 43/24; E21B 43/243; E21B 47/06; E21B 2200/20; E21B 43/164; E21B 41/0064; E21B 49/00; E21B 43/00; E21B 43/16; E21B 43/26; E21B 43/2605; E21B 47/10; E21B 43/003; E21B 49/008; E21B 49/087; E21B 49/0875; E21B 43/168; E21B 43/17; E21B 43/25; E21B 43/40
See application file for complete search history.

(56) References Cited

U.S. PATENT DOCUMENTS

| | | | |
|---|---|---|---|
| 11,022,486 | B2 | 6/2021 | Tong et al. |
| 11,022,618 | B2 | 6/2021 | Sierks et al. |
| 11,027,257 | B2 | 6/2021 | Travolsi et al. |
| 11,031,229 | B2 | 6/2021 | Huang et al. |
| 11,041,849 | B2 | 6/2021 | Wang et al. |
| 11,046,748 | B2 | 6/2021 | Jin |
| 11,049,707 | B2 | 6/2021 | Krechmer et al. |
| 11,052,375 | B2 | 7/2021 | Baumann et al. |
| 11,059,017 | B2 | 7/2021 | Buchner, Sr. et al. |
| 11,065,602 | B2 | 7/2021 | Alayande et al. |
| 11,066,607 | B1 | 7/2021 | Koseoglu |
| 11,072,686 | B2 | 7/2021 | Veneman et al. |
| 11,078,093 | B2 | 8/2021 | Cwiertny et al. |
| 11,083,990 | B2 | 8/2021 | Shigaki et al. |
| 11,091,647 | B2 | 8/2021 | Hagimoto et al. |
| 11,097,226 | B2 | 8/2021 | Nair et al. |
| 11,099,115 | B2 | 8/2021 | Pejcinovic et al. |
| 11,101,126 | B2 | 8/2021 | Liu et al. |
| 11,106,843 | B2 | 8/2021 | Ma et al. |
| 11,123,684 | B2 | 9/2021 | Puxty et al. |
| 11,131,615 | B2 | 9/2021 | Savoy et al. |
| 11,133,169 | B2 | 9/2021 | Jones et al. |
| 11,133,558 | B2 | 9/2021 | Tokuno et al. |
| 11,136,453 | B2 | 10/2021 | Cwiertny et al. |
| 11,137,394 | B2 | 10/2021 | Chen et al. |
| 11,148,119 | B2 | 10/2021 | Fortner et al. |
| 11,156,582 | B2 | 10/2021 | Wang et al. |
| 11,161,745 | B2 | 11/2021 | Mu et al. |
| 11,174,722 | B2 | 11/2021 | Wang et al. |
| 11,179,871 | B2 | 11/2021 | Li |
| 11,181,501 | B2 | 11/2021 | Vellaisamy et al. |
| 11,185,842 | B2 | 11/2021 | Okumura et al. |
| 11,186,894 | B2 | 11/2021 | Wang et al. |
| 11,202,587 | B2 | 12/2021 | Plaxco et al. |
| 11,203,749 | B2 | 12/2021 | Madison et al. |
| 11,207,633 | B2 | 12/2021 | Meirav et al. |
| 11,208,453 | B2 | 12/2021 | Weiss |
| 2010/0250215 | A1* | 9/2010 | Kennon .................. G06F 30/23 703/10 |
| 2013/0262069 | A1 | 10/2013 | Leonard |
| 2022/0178252 | A1 | 6/2022 | Hu et al. |
| 2023/0340876 | A1* | 10/2023 | Luo .................... G01N 33/2841 |

FOREIGN PATENT DOCUMENTS

| | | | | |
|---|---|---|---|---|
| CA | 2858319 | | 6/2013 | |
| CN | 115618768 A | * | 1/2023 | |
| CN | 117470708 A | * | 1/2024 | |
| CN | 117494452 A | * | 2/2024 | ............. G06F 30/20 |
| WO | WO-2018102732 A1 | * | 6/2018 | ............. G01V 1/345 |
| WO | WO-2022173375 A1 | * | 8/2022 | |

OTHER PUBLICATIONS

Sharma et al., "Impact of Total Organic 1-20 Carbon on Adsorption Capacity, In-Place Hydrocarbons, and Ultimate Recovery: A Case Study of the Duvernay Formation in Alberta, Canada," Proceedings of the 2018 Abu Dhabi International Petroleum Exhibition & Conference held in Abu Dhabi, UAE, Nov. 12, 2018, 22 pages.

International Search Report and Written Opinion in International Appln. No. PCT/US2024/015535, mailed on Jun. 3, 2024, 17 pages.

Akkutlu et al., "Multi-Scale Gas Transport in Shales with Local Kerogen Heterogeneities," SPE Journal, Dec. 2012, 17(4):1002-1011, 10 pages.

Ambrose et al., "Shale Gas-in-place Calculations Part I—New Pore-Scale Considerations," SPE Journal. Mar. 2012, 17(1):219-229, 11 pages.

Arumugam, "High-Pressure Adsorption of Pure Coalbed Gases on Dry Coals," Thesis for the degree of Master of Science, Oklahoma State University, Dec. 2004, 127 pages.

Brunauer et al., "Adsorption of Gases in Multimolecular Layers," Journal of the American Chemical Society, Feb. 1938, 60(2):309-319, 11 pages.

Dogru et al., "A Next-Generation Parallel Reservoir Simulator for Giant Reservoirs," SPE Reservoir Simulation Symposium, Feb. 2009, 29 pages.

Langmuir, "The adsorption of gases on plane surfaces of glass, mica and platinum," Journal of the American Chemical society 40.9, Sep. 1918, 1361-1403, 43 pages.

Mavor et al., "Measurement and evaluation of isotherm data," Proceedings of 65th Annual Technical Conference and Exhibition of the Society of Petroleum Engineers, SPE 20728, Sep. 1990, 157-170, 14 pages.

Passey et al., "From oil-prone source rock to gas-producing shale reservoir-geologic and petrophysical characterization of unconventional shale-gas reservoirs," International oil and gas conference and exhibition in China, OnePetro, Jun. 2010, 29 pages.

Reich et al., "Adsorption of Methane, Ethane, And Ethylene Gases And Their Binary And Ternary Mixtures And Carbon Dioxide On Activated Carbon At 212-301 K And Pressures To 35 Atmospheres," Industrial and Engineering Chemistry Process Design and Development, Jul. 1980, 19(3), 336-344, 9 pages.

Santos et al., "Laboratory Measurement of Sorption Isotherm Under Confining Stress with Pore-Volume Effects," SPE International, SPE 162595, Nov. 2012, 12 pages.

Seidle et al., "The Impact of Undersaturation on Coal Gas Economics," SPE International, SPE 107731, Apr. 2007, 12 pages.

Silin et al., "Shale gas: Nanometer-scale observations and well modelling," Journal of Canadian Petroleum Technology 51.06, Nov. 2012, 464-475, 12 pages.

Sing et al., "Reporting Physisorption Data for Gas/Solid Systems with Special Reference to the Determination of Surface Area and Porosity (Recommendations 1984)," Pure and Applied Chemistry, Jan. 1985, 57(4):603-619, 17 pages.

Vermesse et al., "Gas adsorption on zeolites at high pressure," Langmuir, Aug. 1996, 12(17):4190-4196, 7 pages.

Yu et al., "Evaluation of Gas Adsorption in Marcellus Shale," SPE International, SPE 170801-MS, Oct. 2014, 16 pages.

* cited by examiner

FIG. 1

(a) Monolayer Langmuir Adsorption
FIG. 2A (b) Multilayer BET Adsorption
FIG. 2B

MODELING GAS DESORPTION IN A SUBSURFACE RESERVOIR

TECHNICAL FIELD

The present disclosure relates to modeling gas desorption in a subsurface reservoir.

BACKGROUND

Subterranean reservoirs can hold a gas as a free gas in macro pores. A significant portion of the gas can also be stored as sorbed gas. In organic porous materials, gas can be stored as a compressed fluid inside the pores, or it can be taken up by the solid. The molecules that are taken up by the solid either enter the macromolecular openings of the solid (e.g., micro-pores) or remain on the outside of these openings attached to the larger (e.g., meso- and macro-) pore walls. These phenomena are termed absorption (or dissolution) and adsorption, respectively. When the gas absorption and adsorption occur simultaneously, for example in coal seams and organic-rich resource shales, the gas-storage process is termed sorption. Adsorption at a gas/solid interface can be referred to as the enrichment of one or more components in an interfacial layer. For example, the organic matter in a shale has a strong adsorption potential due to large surface area and an affinity to methane.

It is important to estimate the amounts of compressed (or free) and sorbed natural gases in a subterranean reservoir under the subsurface conditions (e.g., pressure and temperature). The total amount of gas in the reservoir represents the gas in place, which is a critical property used to evaluate the economic value of unconventional resources.

SUMMARY

This specification describes an approach to modeling gas desorption in a subterranean reservoir. In unconventional gas resources such as coal and organic-rich shale, a sorbed gas phase can be an important component of storage and transport calculations. The quantification of original adsorbed gas in place (OAGIP) and how it contributes to the total production of the reservoir represent important factors to achieve reliable evaluation of unconventional resources. The estimation of total original gas in place (OGIP), including the adsorbed gas volume, can be fundamental to the assessment of the economic viability of organic-rich reservoirs. The estimation of OGIP reinforces reports of gas reserves and can be vital to various reservoir engineering analyses, for example, history matching, production forecasting, reservoir modeling and reconciling with an estimated ultimate recovery (EUR) of a reservoir.

In one aspect, a method for modeling gas desorption in a subterranean reservoir includes measuring a gas sorption parameter using a crushed core sample from the subterranean reservoir; computing a gas storage capacity of the subterranean reservoir at an initial reservoir pressure based on the gas sorption parameter; generating a three-dimensional (3D) distribution of total organic carbon (TOC) in the subterranean reservoir; estimating a 3D distribution of original adsorbed gas in place of the subterranean reservoir by correlating the gas storage capacity with the 3D distribution of TOC; and predicting the amount of gas desorbed from the subterranean reservoir as the reservoir is depleted.

In one aspect, one or more non-transitory machine-readable storage devices storing instructions for modeling gas desorption in a subterranean reservoir, the instructions being executable by one or more processing devices to cause performance of operations including accessing, from a data store, values of a measured gas sorption parameter for the subterranean reservoir; computing a gas storage capacity of the subterranean reservoir at an initial reservoir pressure based on the values of the measured gas sorption parameter; generating a three-dimensional (3D) distribution of total organic carbon (TOC) in the subterranean reservoir; estimating a 3D distribution of original adsorbed gas in place (OAGIP) of the subterranean reservoir by correlating the gas storage capacity with the 3D distribution of TOC; and predicting the amount of gas desorbed from the subterranean reservoir as the reservoir is depleted.

In one aspect, a system for modeling gas desorption of a subterranean reservoir includes at least one processor, and a memory storing instructions that, when executed by the at least one processor, cause the at least one processor to perform operations including accessing, from a data store, values of a measured gas sorption parameter for the subterranean reservoir; computing a gas storage capacity of the subterranean reservoir at an initial reservoir pressure based on the values of the measured gas sorption parameter; generating a three-dimensional (3D) distribution of total organic carbon (TOC) in the subterranean reservoir; estimating a 3D distribution of original adsorbed gas in place (OAGIP) of the subterranean reservoir by correlating the gas storage capacity with the 3D distribution of TOC; and predicting the amount of gas desorbed from the subterranean reservoir as the reservoir is depleted.

Embodiments of these systems and methods can include one or more of the following features.

In some embodiments, these aspects further include defining a desorption pressure at which gas in the subterranean reservoir begins to desorb. In some cases, the desorption pressure is user-defined for each cell in the 3D distribution of original adsorbed gas in place. In some cases, the subterranean reservoir is under saturated. In some cases, the subterranean reservoir is saturated. In some cases, the desorption pressure is estimated based on a measured gas sorption property.

In some embodiments, the predicting includes using an isotherm scaled by comparing a Langmuir isotherm with the 3D distribution of original adsorbed gas in place.

In some embodiments, these aspects further include producing hydrocarbons from the subterranean reservoir Certain implementations may have particular advantages. In some implementations, both saturated and under saturated desorption mechanisms can be modeled within the same framework. In some implementations, the desorption pressure can be explicitly defined by the user to control the start of the gas desorption to be at a specific pressure in the model. In some cases, the desorption pressure can be defined on a cell-by-cell basis. In some implementations, initialization of the gas desorption volume can capture the heterogeneity of the subterranean reservoir. In some implementations, different desorption mechanisms can be implemented as a function of the pore pressure depletion while producing from the subterranean reservoir. In some implementations, the adaptive methodology distributes the OAGIP throughout the reservoir which is a main component of the hydrocarbon in place and can be fundamental to the assessment of the economic viability of organic-rich reservoirs. In some implementations, using a desorption mechanism to define the OAGIP provides a robust input into history matching processes which can improve the reliability of dynamic models used to evaluate field development plans.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This specification describes an approach to modeling gas desorption in a subterranean reservoir. In unconventional gas resources such as coal and organic-rich shale, a sorbed gas phase can be an important component of storage and transport calculations. The quantification of original adsorbed gas in place (OAGIP) and how it contributes to the total production of the reservoir represent important factors to achieve reliable evaluation of unconventional resources. The estimation of total original gas in place (OGIP), including the adsorbed gas volume, can be fundamental to the assessment of the economic viability of organic-rich reservoirs. The estimation of OGIP reinforces reports of gas reserves and can be vital to various reservoir engineering analyses, for example, history matching, production forecasting, reservoir modeling and reconciling with an estimated ultimate recovery (EUR) of a reservoir.

Figure 1:
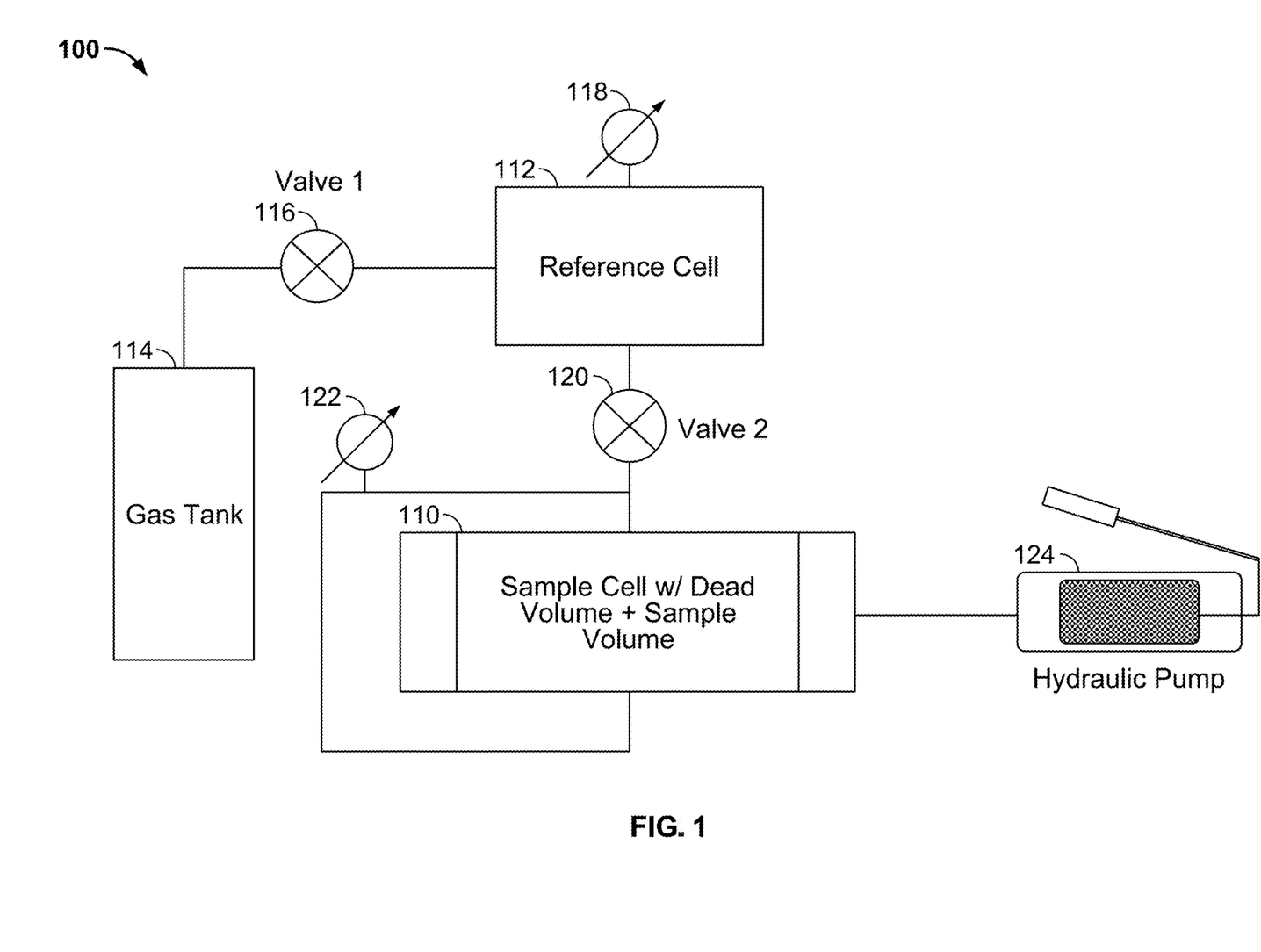
FIG. 1 is an example schematic diagram of an experimental setup to measure gas sorption properties.

FIG. 1 shows an example schematic of an experimental system 100 to estimate gas sorption properties using a crushed core sample. This setup can use a Langmuir lab measurement volumetric technique. The measurements involve determining the amount of gas adsorbed in a sample cell 110 at a specified pressure and temperature after achieving equilibrium at the specified conditions. Determining the amount of gas adsorbed by the crushed core sample can be mainly based on a material balance and Boyle's law. Multiple measurements can be made at multiple values of pressure with a constant temperature.

At each specified pressure, a reference cell 112 can be charged with a measurement gas (e.g., helium, nitrogen, or methane) supplied from a gas tank 114. A first valve 116 located between the gas tank 114 and the reference cell 112 can control the flow of the measurement gas into the reference cell 112. A first pressure gauge 118 can measure the pressure within the reference cell. The reference cell can be connected to the sample cell 110. A second valve 120 can control the flow of gas between the sample cell 110 and the reference cell 112. A second pressure gauge 122 can measure the pressure within the sample cell. The gas in the reference cell 112 can be allowed to flow into the sample cell 110 where the gas expands and is sorbed by the sample until the gas pressures in the reference cell 112 and the sample cell 110 reach equilibrium. The gas pressure is monitored and recorded with the pressure gauges 118, 122 until the sorption is completed and the pressure stabilizes. This procedure of charging the reference cell 112 and subsequently allowing the reference cell 112 and the sample cell 110 to equilibrate with each other can be repeated several times at multiple pressure values. The sample can be subjected to a constant confining pressure throughout the process by use of a hydraulic pump 124, allowing the measurements to be performed under a controlled confining stress or, if desired, under the reservoir stress conditions.

The estimate of gas-storage capacity can then be obtained as a function of pressure and reported, for example, as a volume of adsorbed gas per unit mass of source rock (e.g., standard cubic feet of gas per ton of source rock, scf/ton).

At each specified pressure value, some of the gas expanded in the sample cell can be sorbed (both adsorbed and absorbed) inside the particles of the crushed core sample, and the remainder of the gas can exist as a free gas phase filling the entire void volume inside the sample cell. This total amount of gas measured (e.g., sorbed and free gas) is referred to as the Gibbs adsorption. To measure only the gas sorbed by the sample the total amount of gas measured should be corrected to remove the excess (free) gas amount, known as the Gibbs correction. The Gibbs correction can be calculated using the compressibility equation of state (EOS) from the newly reached equilibrium conditions at each specified pressure value in the sample cell. Following this method, the reported gas storage capacity represents the sorbed gas volume only.

To simulate gas production in subterranean reservoirs, an accurate model of gas adsorption can be critical. There are many types of adsorption and the shape of an adsorption isotherm can be closely related to the properties of the adsorbate (e.g., a gas), the solid adsorbent (e.g., a shale), and on the pore-space geometry. Some commonly applied adsorption models for subterranean reservoirs such as shale gas reservoirs are the Langmuir isotherm and the Brunauer, Emmett and Teller (BET) isotherm.

Figure 2A:
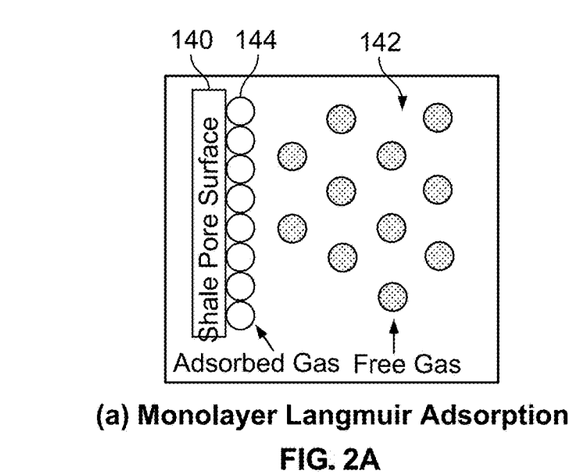
FIGS. 2A-2B are illustrations of gas adsorption.
Figure 2B:
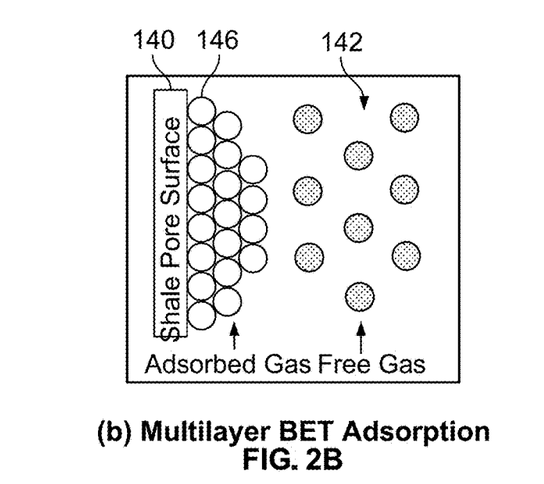

FIG. 2A-2B illustrate example gas adsorption models. FIG. 2A depicts monolayer adsorption, which is assumed by the Langmuir adsorption isotherm model. A porous surface 140 such as shale is in the presence of molecules of a free gas 142. A single layer of gas molecules 144 adhere to the porous surface 140. FIG. 2B depicts a multilayer adsorption which can be assumed when using a BET adsorption isotherm model. In this case, multiple layers of gas molecules 146 adhere to the porous surface 140 when in the presence of a free gas 142.

Langmuir natural-gas sorption parameters (e.g., $V_L$ and $P_L$) of a subterranean reservoir can be estimated using laboratory measurement techniques such as depicted in FIG. 1. $V_L$ is a Langmuir volume that determines the maximum volumetric capacity of adsorbed gas at a hypothetical infinite pressure. $P_L$ determines the shape of an adsorption curve and accordingly it represents the rate of adsorbed gas release. Mathematically, $P_L$ is equivalent to the pressure at one half of $V_L$. In practice, $V_L$ and $P_L$ can be obtained from methane adsorption isotherm tests performed on crushed core samples; both parameters are correlated with adsorbed gas storage capacity $G_c$ at a specific reservoir pressure P using the Langmuir equation:

$$G_c = V_L \frac{P}{P+P_L}. \quad (1)$$

Figure 3:
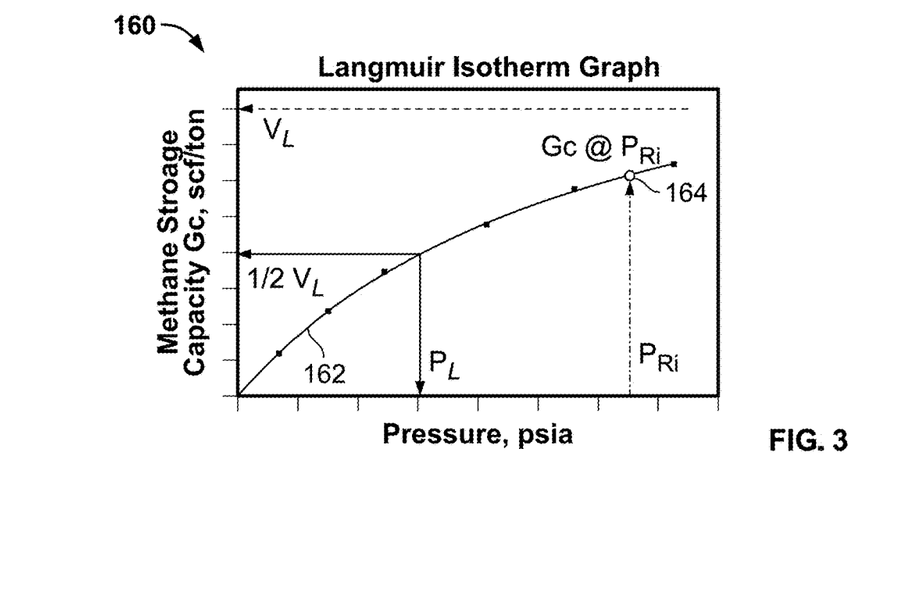
FIG. 3 is an example plot for determining a gas storage capacity of a subterranean reservoir.

FIG. 3 shows an example plot 160 of a Langmuir isotherm 162. In this example, several measurements of adsorbed methane gas storage capacity from a crushed core sample are plotted at their respective specified pressures. Using the measurements and the Langmuir equation (equation 1), values of $V_L$ and $P_L$ can be estimated. Once the values of $V_L$ and $P_L$ are obtained the isotherm 162 can be plotted. For a given initial pressure of the subterranean reservoir, $P_{Ri}$, the initial gas storage capacity of the reservoir $G_c$ 164 can be estimated.

Figure 4:
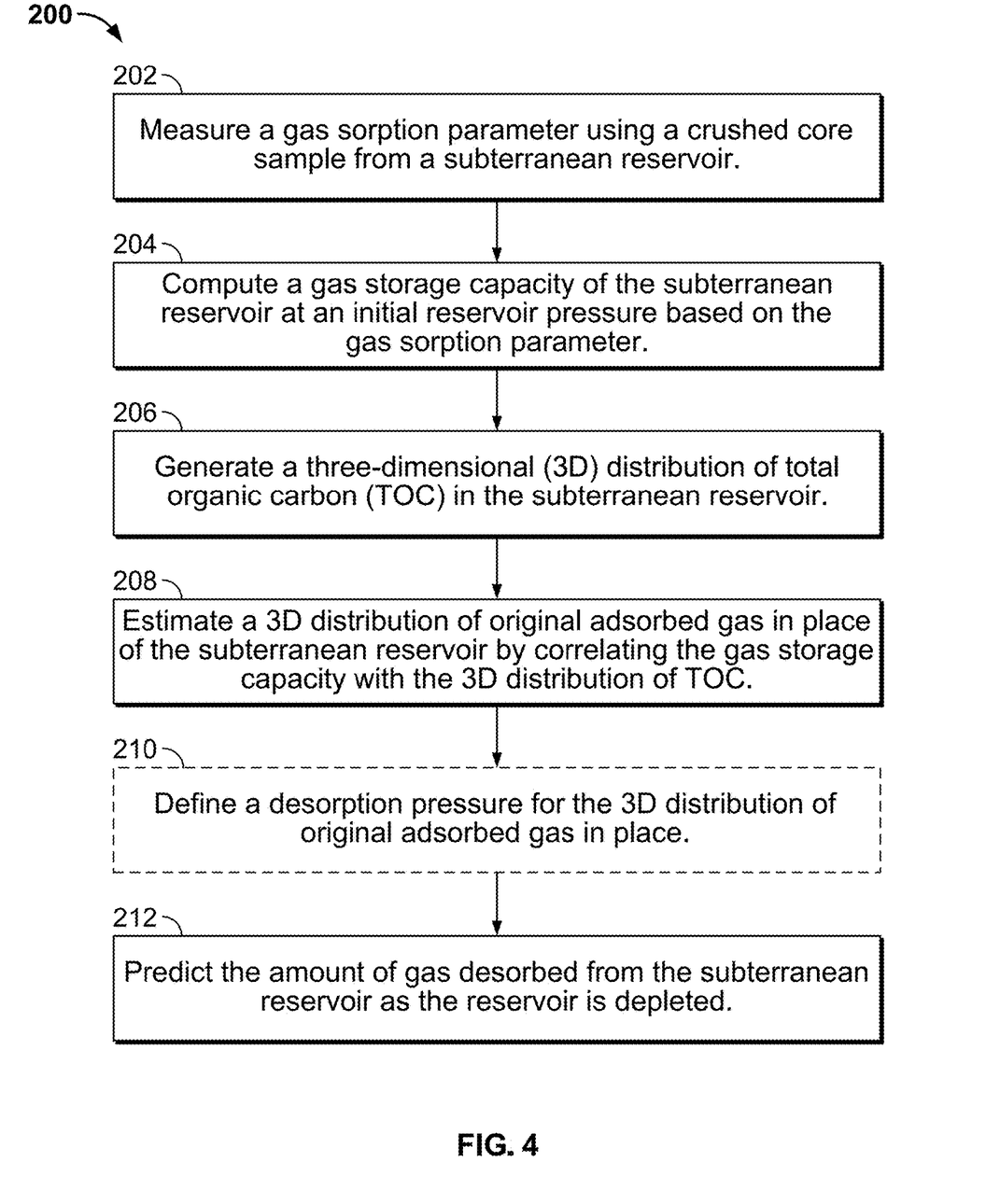
FIG. 4 is an example flow chart of a method for modeling gas desorption in a subterranean reservoir.

FIG. 4 shows an example flow chart of a method 200 for modeling the gas desorption of a subterranean reservoir. Gas sorption parameters can be measured using a crushed core sample from a subterranean reservoir (step 202). For example, laboratory experiments such as depicted in FIG. 1 can be used to measure gas sorption at specified pressure and temperature conditions. Based on the measured gas sorption parameters, a gas storage capacity, $G_c$, at an initial reservoir condition can be computed (step 204). In some implementations, a Langmuir isotherm can be generated such as is depicted in the plot of FIG. 3 to determine the gas storage capacity of the subterranean reservoir.

The gas storage capacity, $G_c$, at an initial reservoir pressure ($P_{Ri}$) can have a good correlation with a total organic carbon (TOC) content of the subterranean reservoir. A three-dimensional (3D) distribution of the TOC can be generated for the subterranean reservoir (step 206).

The 3D distribution of TOC is generated using TOC petrophysical well log data at the well level calibrated with measured TOC lab data. A 3D modeling package can be used to interpolate the available TOC log data to predict the TOC values in between existing wells using known petrophysical modeling stochastic algorithms. For example, the 3D TOC distribution can be a static petrophysical distribution of TOC. In some implementations, the 3D distribution of TOC can be generated as a mathematical function of other 3D petrophysical distributions based on existing correlations. For example, TOC is a function of rock density, porosity, and/or rock maturity.

A 3D distribution of original gas adsorbed in place (OGAIP) for the subsurface reservoir can be estimated by correlating the 3D TOC distribution with the gas storage capacity of the reservoir at the initial reservoir pressure $P_{Ri}$ (step 208). The correlation can be generated using many core samples cut from the subsurface reservoir. The TOC content is measured and recorded for each sample. The adsorbed gas storage capacity $G_c$ as function of pressure is measured, for example, by an apparatus as shown in FIG. 1. The measured $G_c$ value at specific $P_{Ri}$ is recorded and plotted versus the sample TOC. The best fit trend represents the correlation between TOC and $G_c$. In some implementations, the OAGIP can be specified for each cell in the 3D distribution. In some implementations, the OAGIP can be estimated utilizing reservoir rock density or reservoir rock maturity.

Figure 5:
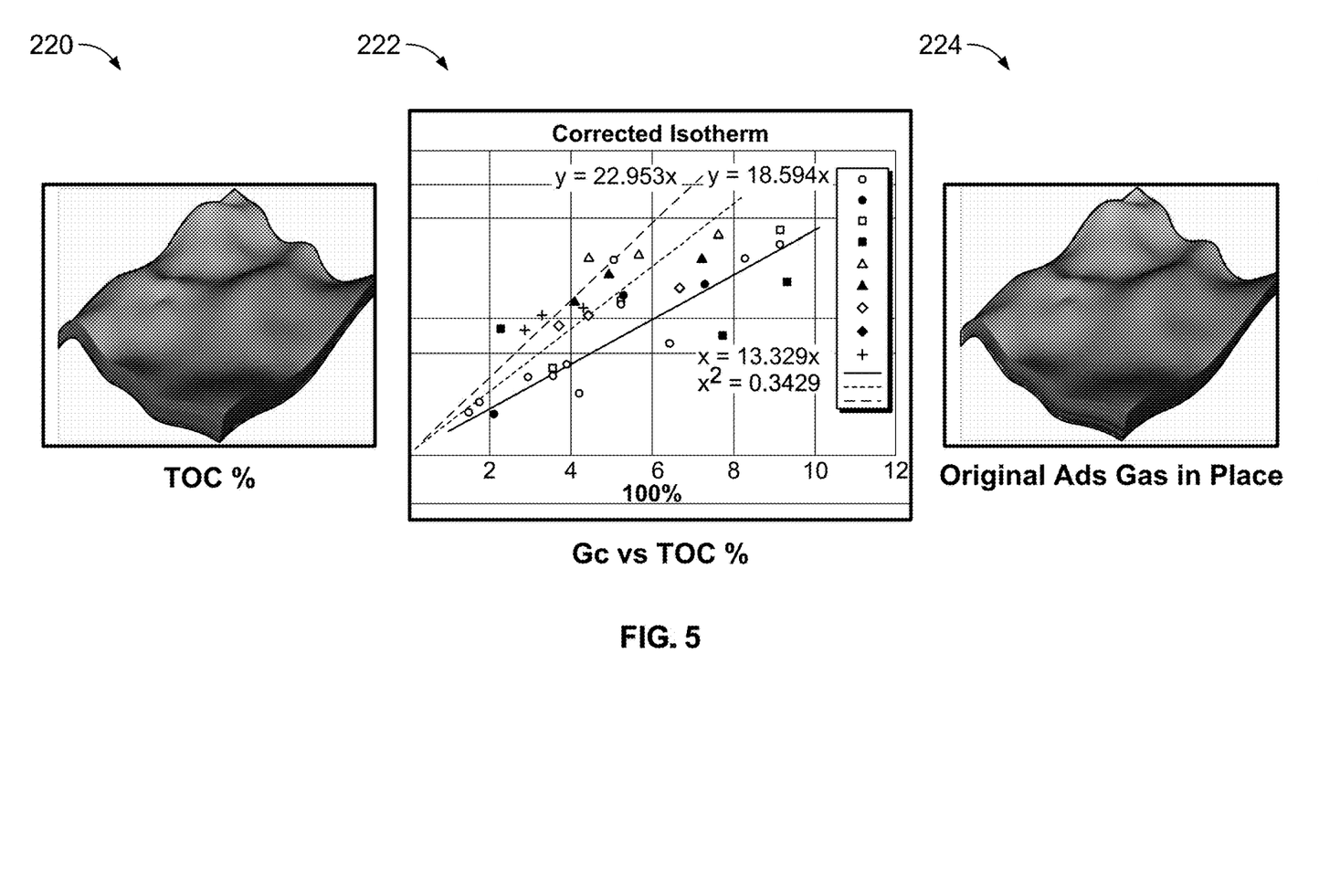
FIG. 5 is an illustration of an example method for determining an original adsorbed gas in place.

FIG. 5 shows an example illustration of the process of estimating the 3D distribution of OAGIP. The first plot 220 shows a 3D distribution of total organic carbon that can be generated for the subsurface reservoir. The second plot 222 demonstrates how the gas storage capacity $G_c$ is correlated with the TOC to obtain the original adsorbed gas in place. The y-axis of plot 222 shows the adsorbed gas storage capacity $G_c$ measured at initial reservoir pressure $P_{Ri}$. The different lines of plot 222 represent different correlation values, (e.g., high, mid, and low) that can cover the uncertainty range of the correlation based on all of the available measured data. In some implementations, each cell of the 3D distribution of TOC can be correlated with a gas storage capacity. The third plot 224 shows a representation of the 3D distribution of the original adsorbed gas in place for the subsurface reservoir.

A desorption pressure can be defined for the 3D distribution of original adsorbed gas in place (step 210). A subterranean reservoir holding a maximum possible amount of gas for the current reservoir pressure and temperature can be said to be saturated whereas a subterranean reservoir holding less than a theoretical maximum can be characterized as under saturated. Under saturated reservoirs can be filled with water and require de-pressuring by water production to initiate gas release from the matrix of the reservoir rock. The pressure at which gas first appears can be defined as the desorption pressure, $P_{Des}$.

In some cases, a subterranean reservoir can indicate delayed gas desorption with a tendency toward an under saturated desorption mechanism. For example, a Gas Isotope analysis can indicate late gas desorption where the desorption starts at a lower pressure than the initial reservoir pressure $P_{Ri}$. To simulate such behavior, the method 200 can utilize the under saturated desorption theory where the total adsorbed gas in the subterranean reservoir can be classified into two portions: the first portion represents a non-movable or residual gas desorption volume, and the second portion represents a movable gas desorption volume. The boundary pressure between the two portions can be defined as the value of the desorption pressure, $P_{Des}$. For example, for a subterranean reservoir with an initial reservoir pressure $P_{Ri}$, the sorbed gas in the reservoir may not begin to desorb until the reservoir pressure is lowered to a value of $P_{Des}$. The volume of gas that was not desorbed between $P_{Ri}$ and $P_{Des}$ can then represent the residual desorption volume while the volume of gas desorbed at pressure values below $P_{Des}$ can represent the movable gas desorption volume. The movable gas desorption volume represents the gas that can be produced from the subterranean reservoir.

The amount of gas desorbed from the subterranean reservoir can be predicted as the reservoir is depleted (step 212) by, for example, using an adsorption isotherm. For example, from equation 1, the adsorption isotherm relates the sorbed-gas storage capacity of a porous material, $G_c$, to the pore pressure P. As the reservoir is depleted the pore pressure can decrease. As the pore pressure decreases, the gas storage capacity can also decrease. A decrease in the gas storage capacity can represent the amount of gas that can desorb from the reservoir. As the reservoir pressure changes during depletion of the reservoir from Pressure 1 (P1) to Pressure 2 (P2), where P1>P2, based on the desorption isotherm the amount of the gas storage capacity at P1 will be decreased to a lower amount at P2, this change in the gas storage capacity represents the gas that can release (e.g., desorb) from the rock surfaces.

In some implementations, a representative adsorption isotherm, for example an isotherm that was developed using experimental measurements, can be scaled on a cell-by-cell basis using the estimated 3D distribution of original adsorbed gas in place (OAGIP). The scaling process can compare a gas storage capacity $G_c$ at the initial reservoir pressure $P_{Ri}$ with the estimated OAGIP to define a scaling factor. In some implementations, the scaling factor is defined as the ratio of the gas storage capacity $G_{c1}$ based on the static gas storage capacity and the gas storage capacity $G_{c2}$ determined by the representative adsorption isotherm: $SF=G_{c1}/G_{c2}$, where SF is the scaling factor. A scaling factor can be defined for each cell in the 3D distribution. The scaling factor can be computed during a dynamic modeling initialization process. The representative isotherm can then be modified to define a new scaled isotherm using the scaling factor. In some implementations, a scaled isotherm can be calculated for each cell of a 3D model using the initial reservoir pressure for each respective cell to guide the scaling process. In some implementations, when using a scaled isotherm, the initial distribution of OAGIP and the trend of a Langmuir isotherm are preserved, which can be used to predict gas desorption while simulating reservoir depletion.

Figure 6:
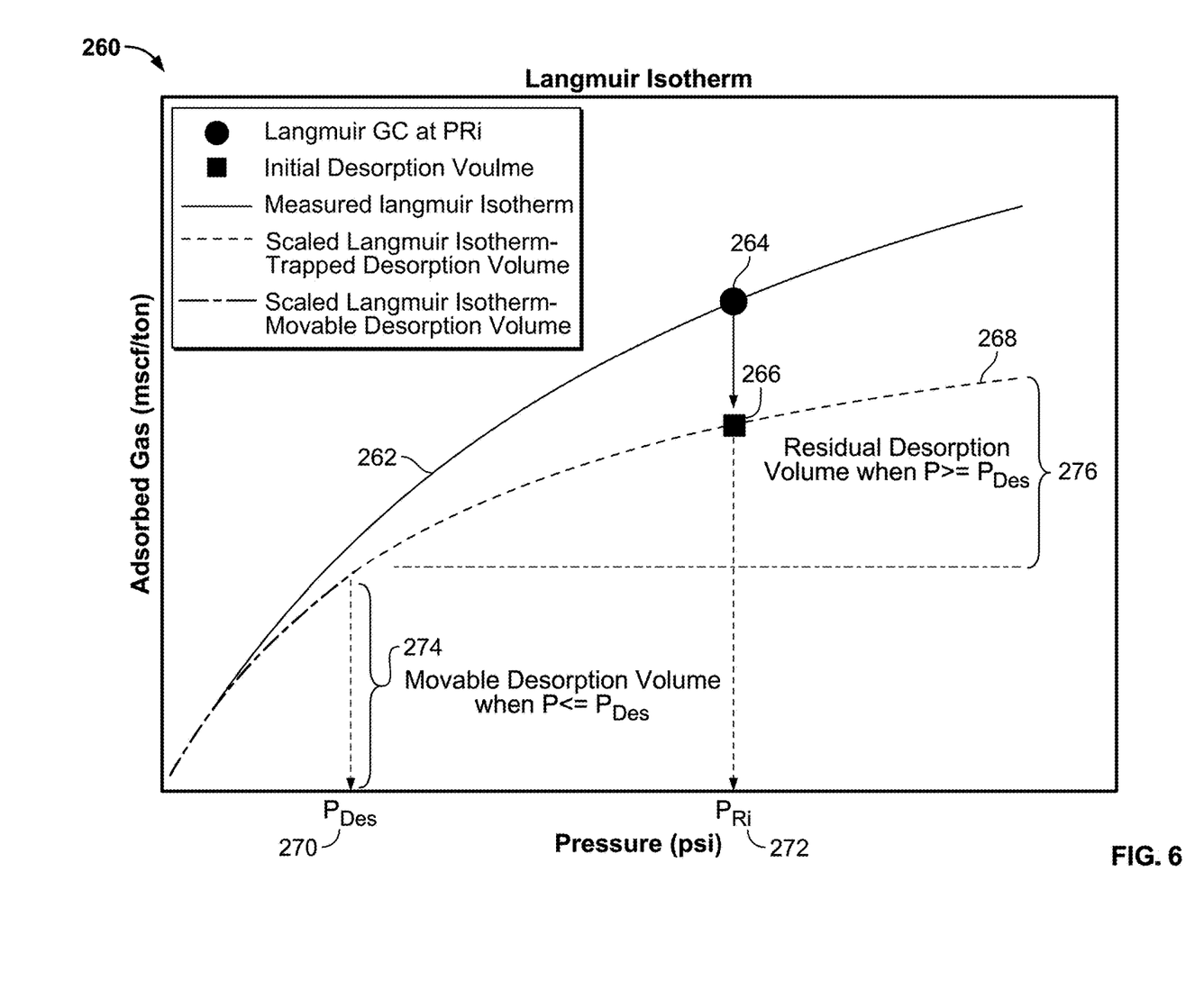
FIG. 6 is an example plot depicting a scaled Langmuir isotherm and desorption pressure.

FIG. 6 is an example plot 260 depicting a scaled Langmuir isotherm and a desorption pressure. In this example, the representative isotherm 262 predicts a larger value of adsorbed gas at the initial reservoir pressure, $G_c$ 264, than is estimated in the original adsorbed gas in place 266. In some cases, the representative isotherm can predict less adsorbed gas storage capacity than is estimated using the OAGIP distribution. The closeness of a predicted gas storage capacity from a representative isotherm to the estimated OAGIP is related to the uncertainty of both quantities. This uncertainty can be affected by, for example, the amount of core sample data generated in the lab or whether a simplified representative isotherm is used to cover a wide range of desorption storage capacities. A scaling factor can be computed using the value of $G_c$ 264 and the value of OAGIP 266 to define a scaled Langmuir isotherm 268. This scaling process can be done for each cell in the 3D model of OAGIP. A scaling factor can be computed for each cell and reported to validate the magnitude of the scaling process.

In some implementations, a desorption pressure can be defined. In FIG. 6 the desorption pressure, $P_{Des}$ 270, is less than the initial reservoir pressure, $P_{Ri}$ 272. The movable desorption volume 274 can be represented by the gas storage capacity for pressures less than $P_{Des}$ 270, and the residual desorption volume can be represented by the gas storage capacity for pressures between $P_{Des}$ 270 and $P_{Ri}$ 272.

In some implementations, the desorption pressure can be specified explicitly by a user. In some implementations, the desorption pressure can be estimated through various methods, for example, direct laboratory measurements, geochemistry isotope analysis, or well performance analysis. In some cases, the desorption pressure can be defined as a history matching parameter while calibrating a dynamic model. In some implementations, a desorption pressure can be specified for each cell of a 3D model. In some implementations, the desorption pressure can be an engineering control to control when the gas desorption begins in the model as the reservoir depletion is simulated. In some implementations, the desorption pressure can be used to control how the gas desorption contributes to production and the magnitude of the contribution.

In some implementations, defining a desorption pressure can model both saturated and under saturated desorption mechanisms within the same model framework. If $P_{Des}$ is defined equal to the initial reservoir pressure $P_{Ri}$, this can represent a saturated desorption mechanism, and the release of the desorbed gas can start immediately with the production of the reservoir. Whereas if $P_{Des}$ is less than $P_{Ri}$, the system can represent an under saturated desorption mechanism where the desorption may not start until the reservoir pressure has declined to the level of $P_{Des}$. In this case, the incremental desorbed gas volume from $P_{Ri}$ to $P_{Des}$ can be considered as a residual desorbed volume and may not contribute into production from the reservoir.

Figure 7:
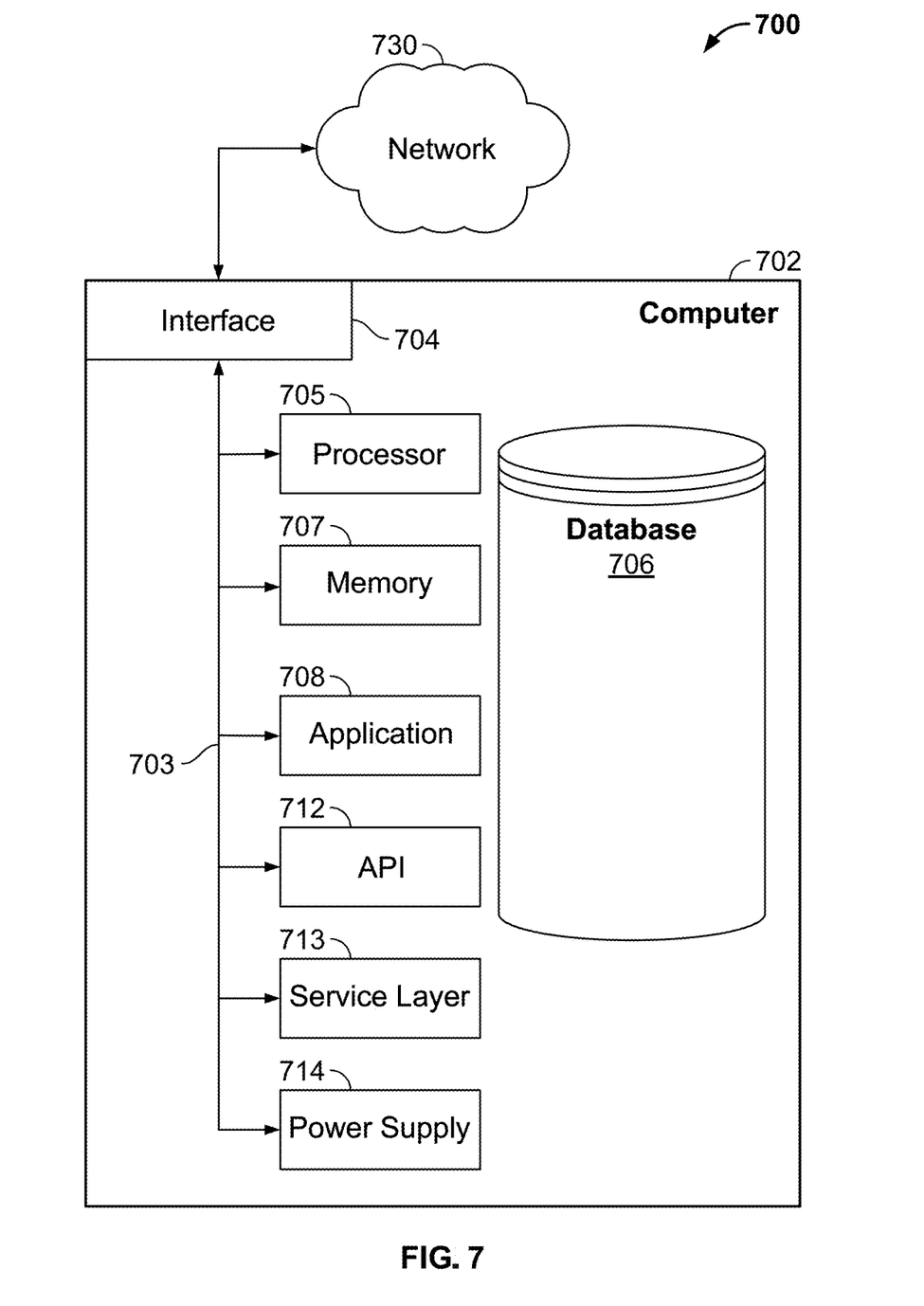
FIG. 7 is a block diagram illustrating an example computer system used to provide computational functionalities associated with described algorithms, methods, functions, processes, flows, and procedures according to some implementations of the present disclosure.

FIG. 7 is a block diagram of an example computer system 700 used to provide computational functionalities associated with described algorithms, methods, functions, processes, flows, and procedures described in the present disclosure, according to some implementations of the present disclosure. The illustrated computer 702 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 702 can include input devices such as keypads, keyboards, and touch screens that can accept user information. Also, the computer 702 can include output devices that can convey information associated with the operation of the computer 702. The information can include digital data, visual data, audio information, or a combination of information. The information can be presented in a graphical user interface (UI) (or GUI).

The computer 702 can serve in a role as a client, a network component, a server, a database, a persistency, or components of a computer system for performing the subject matter described in the present disclosure. The illustrated computer 702 is communicably coupled with a network 730. In some implementations, one or more components of the computer 702 can be configured to operate within different environments, including cloud-computing-based environments, local environments, global environments, and combinations of environments.

At a high level, the computer 702 is an electronic computing device operable to receive, transmit, process, store, and manage data and information associated with the described subject matter. According to some implementations, the computer 702 can also include, or be communicably coupled with, an application server, an email server, a web server, a caching server, a streaming data server, or a combination of servers.

The computer 702 can receive requests over network 730 from a client application (for example, executing on another computer 702). The computer 702 can respond to the received requests by processing the received requests using software applications. Requests can also be sent to the computer 702 from internal users (for example, from a command console), external (or third) parties, automated applications, entities, individuals, systems, and computers.

Each of the components of the computer 702 can communicate using a system bus 703. In some implementations, any, or all the components of the computer 702, including hardware or software components, can interface with each other or the interface 704 (or a combination of both), over the system bus 703. Interfaces can use an application programming interface (API) 712, a service layer 713, or a combination of the API 712 and service layer 713. The API 712 can include specifications for routines, data structures, and object classes. The API 712 can be either computer-language independent or dependent. The API 712 can refer to a complete interface, a single function, or a set of APIs.

The service layer 713 can provide software services to the computer 702 and other components (whether illustrated or not) that are communicably coupled to the computer 702. The functionality of the computer 702 can be accessible for all service consumers using this service layer. Software services, such as those provided by the service layer 713, can provide reusable, defined functionalities through a defined interface. For example, the interface can be software written in JAVA, C++, or a language providing data in extensible markup language (XML) format. While illustrated as an integrated component of the computer 702, in alternative implementations, the API 712 or the service layer 713 can be stand-alone components in relation to other components of the computer 702 and other components communicably coupled to the computer 702. Moreover, any or all parts of the API 712 or the service layer 713 can be implemented as child or sub-modules of another software module, enterprise application, or hardware module without departing from the scope of the present disclosure.

The computer 702 includes an interface 704. Although illustrated as a single interface 704 in FIG. 7, two or more interfaces 704 can be used according to particular needs, desires, or particular implementations of the computer 702 and the described functionality. The interface 704 can be used by the computer 702 for communicating with other systems that are connected to the network 730 (whether illustrated or not) in a distributed environment. Generally, the interface 704 can include, or be implemented using, logic encoded in software or hardware (or a combination of software and hardware) operable to communicate with the network 730. More specifically, the interface 704 can include software supporting one or more communication protocols associated with communications. As such, the network 730 or the interface's hardware can be operable to communicate physical signals within and outside of the illustrated computer 702.

The computer 702 includes a processor 705. Although illustrated as a single processor 705 in FIG. 7, two or more processors 705 can be used according to particular needs, desires, or particular implementations of the computer 702 and the described functionality. Generally, the processor 705 can execute instructions and can manipulate data to perform the operations of the computer 702, including operations using algorithms, methods, functions, processes, flows, and procedures as described in the present disclosure.

The computer 702 also includes a database 706 that can hold data for the computer 702 and other components connected to the network 730 (whether illustrated or not). For example, database 706 can be an in-memory, conventional, or a database storing data consistent with the present disclosure. In some implementations, database 706 can be a combination of two or more different database types (for example, hybrid in-memory and conventional databases) according to particular needs, desires, or particular implementations of the computer 702 and the described functionality. Although illustrated as a single database 706 in FIG. 7, two or more databases (of the same, different, or combination of types) can be used according to particular needs, desires, or particular implementations of the computer 702 and the described functionality. While database 706 is illustrated as an internal component of the computer 702, in alternative implementations, database 706 can be external to the computer 702.

The computer 702 also includes a memory 707 that can hold data for the computer 702 or a combination of components connected to the network 730 (whether illustrated or not). Memory 707 can store any data consistent with the present disclosure. In some implementations, memory 707 can be a combination of two or more different types of memory (for example, a combination of semiconductor and magnetic storage) according to particular needs, desires, or particular implementations of the computer 702 and the described functionality. Although illustrated as a single memory 707 in FIG. 7, two or more memories 707 (of the same, different, or combination of types) can be used according to particular needs, desires, or particular implementations of the computer 702 and the described functionality. While memory 707 is illustrated as an internal component of the computer 702, in alternative implementations, memory 707 can be external to the computer 702.

The application 708 can be an algorithmic software engine providing functionality according to particular needs, desires, or particular implementations of the computer 702 and the described functionality. For example, application 708 can serve as one or more components, modules, or applications. Further, although illustrated as a single application 708, the application 708 can be implemented as multiple applications 708 on the computer 702. In addition, although illustrated as internal to the computer 702, in alternative implementations, the application 708 can be external to the computer 702.

The computer 702 can also include a power supply 714. The power supply 714 can include a rechargeable or non-rechargeable battery that can be configured to be either user- or non-user-replaceable. In some implementations, the power supply 714 can include power-conversion and management circuits, including recharging, standby, and power management functionalities. In some implementations, the power-supply 714 can include a power plug to allow the computer 702 to be plugged into a wall socket or a power source to, for example, power the computer 702 or recharge a rechargeable battery.

There can be any number of computers 702 associated with, or external to, a computer system containing computer 702, with each computer 702 communicating over network 730. Further, the terms "client," "user," and other appropriate terminology can be used interchangeably, as appropriate, without departing from the scope of the present disclosure. Moreover, the present disclosure contemplates that many users can use one computer 702 and one user can use multiple computers 702.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of the invention have been described. Nevertheless, it will be understood that various modifications may be made without departing from the spirit and scope of the invention. For example, the steps of the method 200 can be performed in a different order than shown herein. Accordingly, other embodiments are within the scope of the following claims.

What is claimed is:

1. A method for modeling gas desorption in a subterranean reservoir, the method comprising:
measuring a gas sorption parameter using a crushed core sample from the subterranean reservoir;
computing a gas storage capacity of the subterranean reservoir at an initial reservoir pressure based on the gas sorption parameter;
generating a three-dimensional (3D) distribution of total organic carbon (TOC) in the subterranean reservoir;
estimating a 3D distribution of original adsorbed gas in place of the subterranean reservoir by correlating the gas storage capacity with the 3D distribution of TOC; and
predicting the amount of gas desorbed from the subterranean reservoir as the reservoir is depleted.

2. The method of claim 1, further comprising:
defining a desorption pressure at which gas in the subterranean reservoir begins to desorb.

3. The method of claim 2, wherein, the desorption pressure is user-defined for each cell in the 3D distribution of original adsorbed gas in place.

4. The method of claim 2, wherein the subterranean reservoir is under saturated.

5. The method of claim 2, wherein the subterranean reservoir is saturated.

6. The method of claim 2, wherein the desorption pressure is estimated based on the measuring.

7. The method of claim 1, wherein the predicting comprises using an isotherm scaled by comparing a Langmuir isotherm with the 3D distribution of original adsorbed gas in place.

8. The method of claim 1, further comprising producing hydrocarbons from the subterranean reservoir.

9. One or more non-transitory machine-readable storage devices storing instructions for modeling gas desorption in a subterranean reservoir, the instructions being executable by one or more processing devices to cause performance of operations comprising:
- accessing, from a data store, values of a measured gas sorption parameter for the subterranean reservoir;
- computing a gas storage capacity of the subterranean reservoir at an initial reservoir pressure based on the values of the measured gas sorption parameter;
- generating a three-dimensional (3D) distribution of total organic carbon (TOC) in the subterranean reservoir;
- estimating a 3D distribution of original adsorbed gas in place (OAGIP) of the subterranean reservoir by correlating the gas storage capacity with the 3D distribution of TOC; and
- predicting the amount of gas desorbed from the subterranean reservoir as the reservoir is depleted.

10. The non-transitory machine-readable storage devices of claim 9, wherein the operations further comprise:
- defining a desorption pressure at which gas in the subterranean reservoir begins to desorb.

11. The non-transitory machine-readable storage devices of claim 10, wherein, the desorption pressure is user defined for each cell in the 3D distribution of OAGIP.

12. The non-transitory machine-readable storage devices of claim 10, wherein the subterranean reservoir is under saturated.

13. The non-transitory machine-readable storage devices of claim 10, wherein the subterranean reservoir is saturated.

14. The non-transitory machine-readable storage devices of claim 10, wherein the desorption pressure is estimated based on a measured gas sorption property.

15. The non-transitory machine-readable storage devices of claim 9, wherein the predicting comprises using an isotherm scaled by comparing a Langmuir isotherm with the 3D distribution of original adsorbed gas in place.

16. A system for modeling gas desorption of a subterranean reservoir, the system comprising:
- at least one processor; and
- a memory storing instructions that, when executed by the at least one processor, cause the at least one processor to perform operations comprising:
  - accessing, from a data store, values of a measured gas sorption parameter for the subterranean reservoir;
  - computing a gas storage capacity of the subterranean reservoir at an initial reservoir pressure based on the values of the measured gas sorption parameter;
  - generating a three-dimensional (3D) distribution of total organic carbon (TOC) in the subterranean reservoir;
  - estimating a 3D distribution of original adsorbed gas in place (OAGIP) of the subterranean reservoir by correlating the gas storage capacity with the 3D distribution of TOC; and
  - predicting the amount of gas desorbed from the subterranean reservoir as the reservoir is depleted.

17. The system of claim 16, wherein the operations further comprise:
- defining a desorption pressure at which gas in the subterranean reservoir begins to desorb.

18. The system of claim 17, wherein, the desorption pressure is user-defined for each cell in the 3D distribution of original adsorbed gas in place.

19. The system of claim 17, wherein the subterranean reservoir is under saturated.

20. The system of claim 16, wherein the predicting comprises using an isotherm scaled by comparing a Langmuir isotherm with the 3D distribution of original adsorbed gas in place.

* * * * *